United States Patent
Brown et al.

(10) Patent No.: US 10,675,396 B2
(45) Date of Patent: Jun. 9, 2020

(54) SUCTION DETECTION METHODS AND DEVICES

(71) Applicant: HeartWare, Inc., Miami Lakes, FL (US)

(72) Inventors: Michael C. Brown, Boston, MA (US); Neil Voskoboynikov, Pembroke Pines, FL (US)

(73) Assignee: HeartWare, Inc., Miami Lakes, FL (US)

( * ) Notice: Subject to any disclaimer, the term of this patent is extended or adjusted under 35 U.S.C. 154(b) by 323 days.

(21) Appl. No.: 15/665,718

(22) Filed: Aug. 1, 2017

(65) Prior Publication Data
US 2018/0028738 A1    Feb. 1, 2018

Related U.S. Application Data

(60) Provisional application No. 62/369,295, filed on Aug. 1, 2016.

(51) Int. Cl.
*A61M 1/12*  (2006.01)
*A61M 1/10*  (2006.01)

(52) U.S. Cl.
CPC .......... *A61M 1/122* (2014.02); *A61M 1/1029* (2014.02); *A61M 1/1086* (2013.01);
(Continued)

(58) Field of Classification Search
CPC .... A61M 1/122; A61M 1/1086; A61M 1/101; A61M 1/1031; A61M 2205/3365;
(Continued)

(56) References Cited

U.S. PATENT DOCUMENTS 6,234,772 B1  5/2001  Wampler et al.
7,645,225 B2 *  1/2010  Medvedev ............ A61M 1/101
318/432

(Continued)

FOREIGN PATENT DOCUMENTS

WO  2015195916 A1  12/2015
WO  2016033131 A1  3/2016

OTHER PUBLICATIONS

International Search Report and Written Opinion dated Oct. 20, 2017, for corresponding International Application No. PCT/US2017/044823; International Filing Date: Aug. 1, 2017 consisting of 10-pages.

(Continued)

*Primary Examiner* — Deborah L Malamud
(74) *Attorney, Agent, or Firm* — Christopher & Weisberg, P.A.

(57) ABSTRACT

A method of detecting a suction condition during operation of a rotary blood pump with an inlet connected to a ventricle of the heart of a patient, an outlet connected to an artery of the patient, a rotor, and a control circuit configured maintain the rotor at a set rotational speed. The method includes measuring the rotational speed of the rotor at a plurality of times during each of a plurality of speed measurement intervals. A speed range is determined between a minimum measured speed and a maximum measured speed during each of the plurality of speed measurement intervals. At least one additional parameter relating to the operation of the blood pump is derived. A suction detection signal is generated if both at least one determined speed range is above a speed range limit and the at least one additional parameter is indicative of a suction condition.

8 Claims, 7 Drawing Sheets

(52) U.S. Cl.
CPC ............... *A61M 2205/3334* (2013.01); *A61M 2205/3365* (2013.01)

(58) Field of Classification Search
CPC .... A61M 1/10; A61M 1/125; A61M 2205/04; A61M 2210/125; A61M 1/12; A61M 1/1001; A61B 5/02141; A61B 5/0215; A61B 5/00
See application file for complete search history.

(56) References Cited

U.S. PATENT DOCUMENTS

| | | |
|---|---|---|
| 8,512,013 B2 | 8/2013 | LaRose et al. |
| 8,897,873 B2 | 11/2014 | Schima et al. |
| 8,961,390 B2 | 2/2015 | LaRose et al. |
| 2012/0245681 A1 | 9/2012 | Casas et al. |
| 2014/0100413 A1 | 4/2014 | Casas et al. |
| 2015/0367048 A1 | 12/2015 | Brown et al. |

OTHER PUBLICATIONS

David G. Mason, et al., Reliable Suction Detection for Patients With Rotary Blood Pumps, ASAIO Journal 2008, DOI: 10.1097/MAT.0b013e31817b5b0e.

Shashima Nakahara, et al., Ventricular Arrhythmias After Left Ventricular Assist Device, Advances in Arrhythmia and Electrophysiology, DOI: 10.1161/CIRCEP.113.000113.

Siew-Cheok Ng, et al., Evaluation of Suction Detection During Different Pumping States in an Implantable Rotary Blood Pump, Artificial Organs, 2013 Wiley Periodicals, Inc. and International Center for Artificial Organs and Transplantation.

Oliver Voigt, et al., Suction Detection for the MicroMed DeBakey Left Ventricular Assist Device, ASAIO Journal 2005, DOI: 10.1097/01.mat.0000169118.21639.da.

\* cited by examiner

SUCTION DETECTION METHODS AND DEVICES

CROSS-REFERENCE TO RELATED APPLICATION

This application is related to and claims priority to U.S. Provisional Patent Application Ser. No. 62/369,295, filed Aug. 1, 2016, entitled SUCTION DETECTION METHODS AND DEVICES, the entirety of which is incorporated herein by reference.

STATEMENT REGARDING FEDERALLY SPONSORED RESEARCH OR DEVELOPMENT n/a

TECHNICAL FIELD

The present invention relates to a method and system for detecting suction conditions in a patient having an implantable blood pump.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device or "VAD." Where a VAD is used to assist the pumping action of the left ventricle, the device draws blood from the left ventricle of the heart and discharges the blood into the aorta.

To provide clinically useful assistance to the heart, blood pumps impel blood at a substantial blood flow rate. For an adult human patient, a ventricular assist device may be arranged to pump blood at about 1-10 liters per minute at a differential pressure across the pump of about 10-110 mm Hg, depending on the needs of the patient. The needs of the patient may vary with age, height, and other factors.

If a VAD is operated at an average flow rate in excess of the average inflow rate of blood to the ventricle, the VAD will create a suction condition within the ventricle, wherein the ventricle is collapsed and essentially devoid of blood. This condition is undesirable. For example, in such a condition the wall of the ventricle may collapse in such a way that the wall occludes the pump inlet, causing the flow rate through the pump to decline rapidly, leading to inadequate blood perfusion. Moreover, if a suction condition is maintained for a prolonged period, it can cause damage to the heart. Accordingly, as disclosed, for example, in U.S. Patent Application Publication Nos. 2015/0367048 ("the '048 Publication") and 2014/0100413 ("the '413 Publication"), the disclosures of which are incorporated by reference herein, VAD control systems have been arranged to detect suction conditions. For example, the '048 Publication discloses methods in which the control system associated with the pump acquires data representing flow rate through the pump and examines this data to detect a suction condition. In one embodiment, the control system examines the minimum flow rate occurring during one or more cardiac cycles, the amplitude of the flow rate waveform and the average flow rate to yield a calculated value. The control system may examine a plurality of these calculated values representing several cardiac cycles and determine properties such as the mean, median, mode and standard deviation of such values to determine whether or not a suction condition exists. As disclosed in the '413 Publication, the control system may compare a minimum flow rate occurring during a current cardiac cycle against a threshold which is set based on minima of previous cardiac cycles, and determine that a suction condition exists if the minimum flowrate for the current cardiac cycle is below the threshold. In either case, the control system may respond to detection of a suction condition by altering operation of the pump as, for example, by reducing the set rotational speed of the rotor, in an effort to clear the suction condition, by issuing an alarm signal, or both. Despite these and other improvements in the art, still further improvements would be desirable. For example, systems based on thresholds established during previous cardiac cycles can be susceptible to false alarms when the set rotational speed of the rotor is deliberately changed. In some cases, the suction detection function is disabled during speed changes, during pump startup or both. Moreover, if a suction condition exists immediately after startup of the VAD or when the detection system is re-enabled after being disabled, the thresholds may be set based on conditions prevailing during the suction condition, and the system may ignore the suction condition.

SUMMARY

The present invention advantageously provides a method of detecting a suction condition during operation of a rotary blood pump with an inlet connected to a ventricle of the heart of a patient, an outlet connected to an artery of the patient, a rotor, and a control circuit configured maintain the rotor at a set rotational speed. The method includes measuring the rotational speed of the rotor at a plurality of times during each of a plurality of speed measurement intervals. A speed range is determined between a minimum measured speed and a maximum measured speed during each of the plurality of speed measurement intervals. At least one additional parameter relating to the operation of the blood pump is derived. A suction detection signal is generated if both at least one determined speed range is above a speed range limit and the at least one additional parameter is indicative of a suction condition.

In another aspect of this embodiment, the speed range limit is a function of the set speed during a respective one of the plurality of speed measurement intervals.

In another aspect of this embodiment, the method further includes determining an error signal based on at least one from the group consisting of a difference between the measured speed and the set speed, an integral of such difference over time, and a first derivative of such difference.

In another aspect of this embodiment, generating the suction detection signal includes generating the suction detection signal if (i) occurs during one speed measurement interval at least partially encompassing a cardiac cycle of the patient's heart and (ii) is occurs during the same cardiac cycle of the patient's heart.

In another aspect of this embodiment, the at least one additional parameter includes a duty parameter representing a proportion of time during one or more cardiac cycles of the patient's heart when a flow rate is above a crossover flow rate.

In another aspect of this embodiment, the method further includes repeatedly determining an average flow rate, and wherein the crossover flow rate is a function of the average flow rate.

In another aspect of this embodiment, the crossover flow rate is equal to the average flow rate.

In another aspect of this embodiment, the method further includes comparing the duty parameter to a duty limit constant, and wherein the duty parameter varies directly with the proportion of time the flow rate is above the crossover flow rate.

In another aspect of this embodiment, the method further includes adjusting the set rotational speed of the rotor responsive to the suction detect signal.

In another embodiment, a method of detecting a suction condition during operation of a rotary blood pump with an inlet connected to a ventricle of a heart of a patient, an outlet connected to an artery of the patient, and a control circuit configured to maintain a rotor of the rotary blood pump at a set rotational speed comprises monitoring a flow rate of blood through the pump. A duty parameter representing a proportion of a time during one or more cardiac cycles of the patient's heart when the flow rate is above a crossover flow rate is determined. A suction detect signal is generated based at least in part on the duty parameter.

In another aspect of this embodiment, generating the suction detect signal includes comparing the duty parameter in one or more cardiac cycles with a duty limit corresponding to a set proportion of the time during the one or more cardiac cycles and generating the suction detect signal based at least in part on the comparison.

In another aspect of this embodiment, the method further includes the step of generating the suction detect signal if the duty parameter in one or more cardiac cycles represents a proportion above the set proportion.

In another aspect of this embodiment, generating the suction detect signal is performed if the duty parameter in a single cardiac cycle represents a proportion above the set proportion.

In another aspect of this embodiment, the method further includes deriving at least one additional parameter relating to operation of the blood pump, generating at least one additional signal if the at least one additional parameter is indicative of a suction condition, and altering operation of the blood pump if both the duty cycle signal and the at least one additional signal are generated.

In another aspect of this embodiment, the method further includes deriving at least one additional parameter includes measuring a speed of the pump at a plurality of times during one or more speed measurement intervals at least partially encompassing the one or more cardiac cycles and determining a speed range between a minimum measured speed and a maximum measured speed during each speed measurement interval.

In another aspect of this embodiment, generating at least one additional signal is performed by generating a speed range signal if the speed range exceeds a range limit, and wherein the suction detect signal is generated if both the speed range signal and the duty signal are both generated.

In another aspect of this embodiment, the method further includes determining an average flow rate, and wherein the crossover flow rate is a function of the average flow rate.

In another aspect of this embodiment, the crossover flow rate is equal to the average flow rate.

In another aspect of this embodiment, the method further includes altering operation of the blood pump responsive to the suction detect signal.

In yet another embodiment a ventricular assist device comprises a rotary blood pump having a housing with an inlet and an outlet, an impeller disposed in the housing between the inlet and the outlet, the impeller being configured to impel blood within the housing toward the outlet when rotating, and a motor configured to rotate the impeller. A control circuit is in communication with the blood pump and is configured to determine a rotational speed of the impeller and a flow rate through the pump determine a duty parameter representing a proportion of time during one or more cardiac cycles of a patient's heart when the flow rate is above a crossover flow rate, generate a suction detect signal based at least in part on the duty parameter, and alter operation of the pump responsive to detection of a suction condition.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
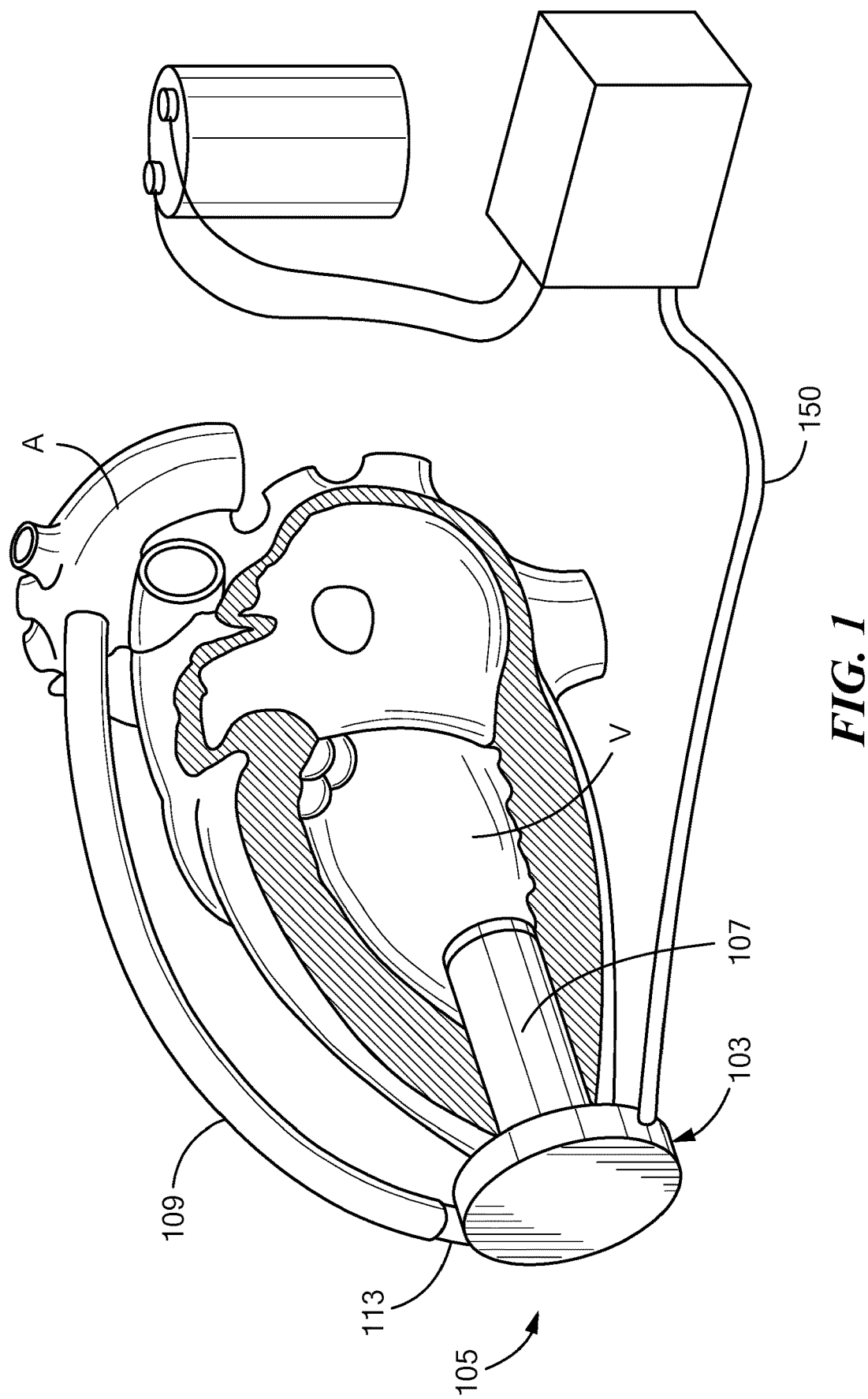
FIG. 1 is a diagrammatic view of a VAD in accordance with one embodiment of the disclosure in conjunction with part of a patient's vascular system.
Figure 2:
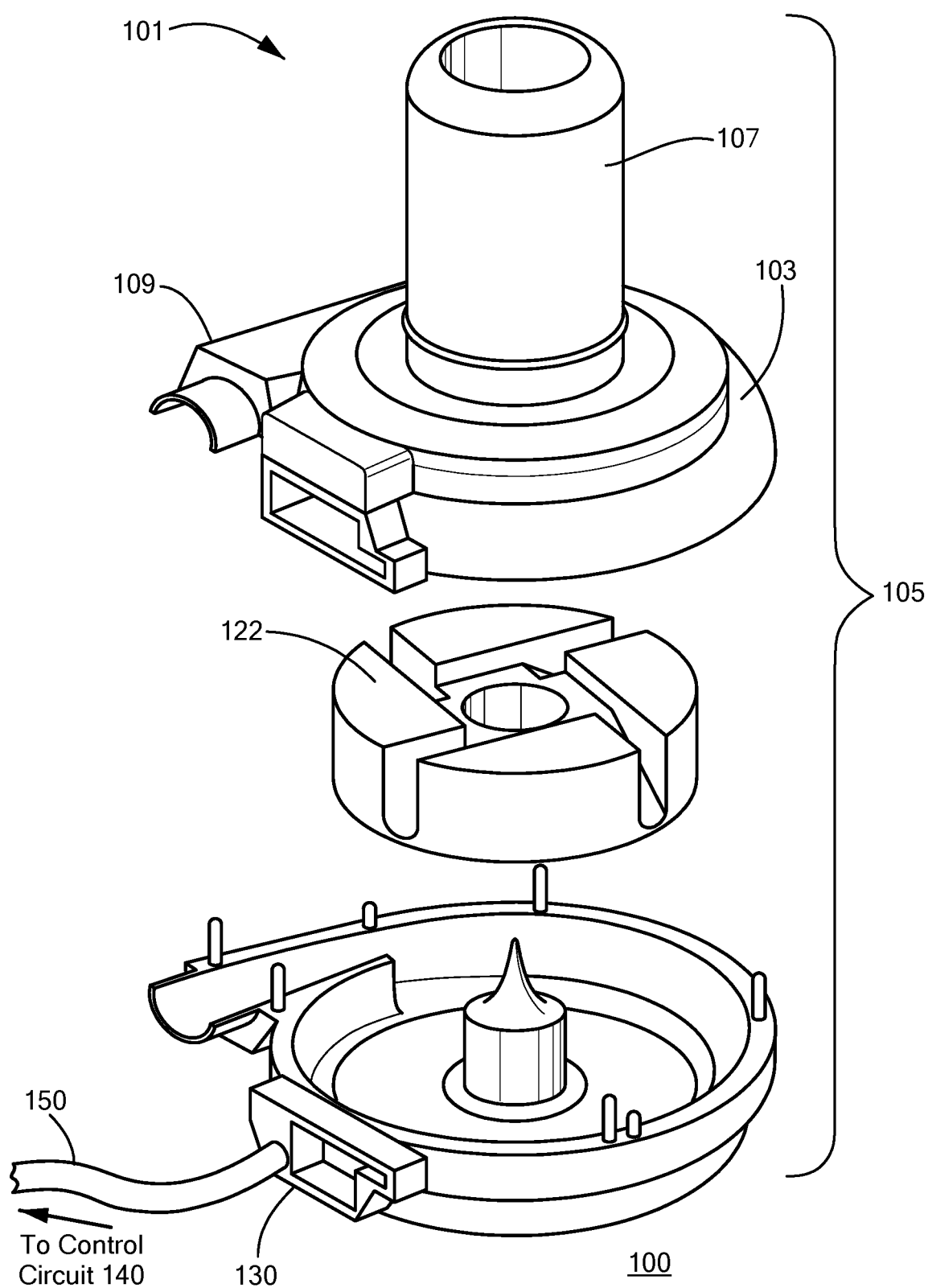
FIG. 2 is an exploded perspective view depicting part of the VAD of FIG. 1.

Now referring to the drawings in which like designators refer to like elements, there is shown in FIGS. 1 and 2 a blood pump VAD and control circuit constructed according to one embodiment of the application. In this embodiment, the pump is a centrifugal pump, such as the HVAD® Pump manufactured by HeartWare Inc. in Miami Lakes, Fla., USA. The HVAD® Pump is further described in U.S. Pat. Nos. 6,234,772 and 8,512,013, the disclosures of which are incorporated by reference. The blood pump 101 includes a housing 105 including interlocking casings to form a closed pumping chamber 103 between them. Blood is supplied to the pump 101 through an axial inlet cannula 107 adapted for apical insertion into a heart ventricle. The cannula 107 is affixed to or may be integral with the housing 105 and is in fluid flow communication with the pumping chamber 103. Blood exits the pumping chamber 103 through an outlet 113 in a direction substantially perpendicular to the longitudinal axis of the inlet cannula 107. As best seen in FIG. 1, the outlet of the housing can be connected to an artery of the patient, such as the aorta, by an outlet cannula 109.

A rotor or pump impeller 122 (FIG. 2) is located within the pumping chamber 103. The rotor incorporates one or more permanent magnets (not shown), and sets of electrical coils (not shown) are disposed in fixed locations within housing 105. The coils and magnets form a motor. In operation, blood entering the cannula 107 from a heart ventricle passes into the pumping chamber 103 where it is engaged by the rotating impeller 122. Blood entering the pumping chamber from the cannula 107 is redirected from axial flow exiting the cannula to a radial flow within which the impeller 122 is submerged.

A power and control cable 150 extends through a feedthrough 130 on the housing, and connects the coils within the housing to a control circuit 140. Control circuit 140 is connected to a source of electrical energy 142, which may include a storage battery, a mains power connection, or both. As further discussed below, control circuit 140 is arranged to energize the coils of the pump in sequence so as to apply a rotating magnetic field within the housing and drive rotor 122 in rotation so that, in operation, the pump draws blood from the left ventricle V of the patient's heart and propels the blood through outflow cannula 109 (FIG. 1) into the patient's aorta.

Figure 3:
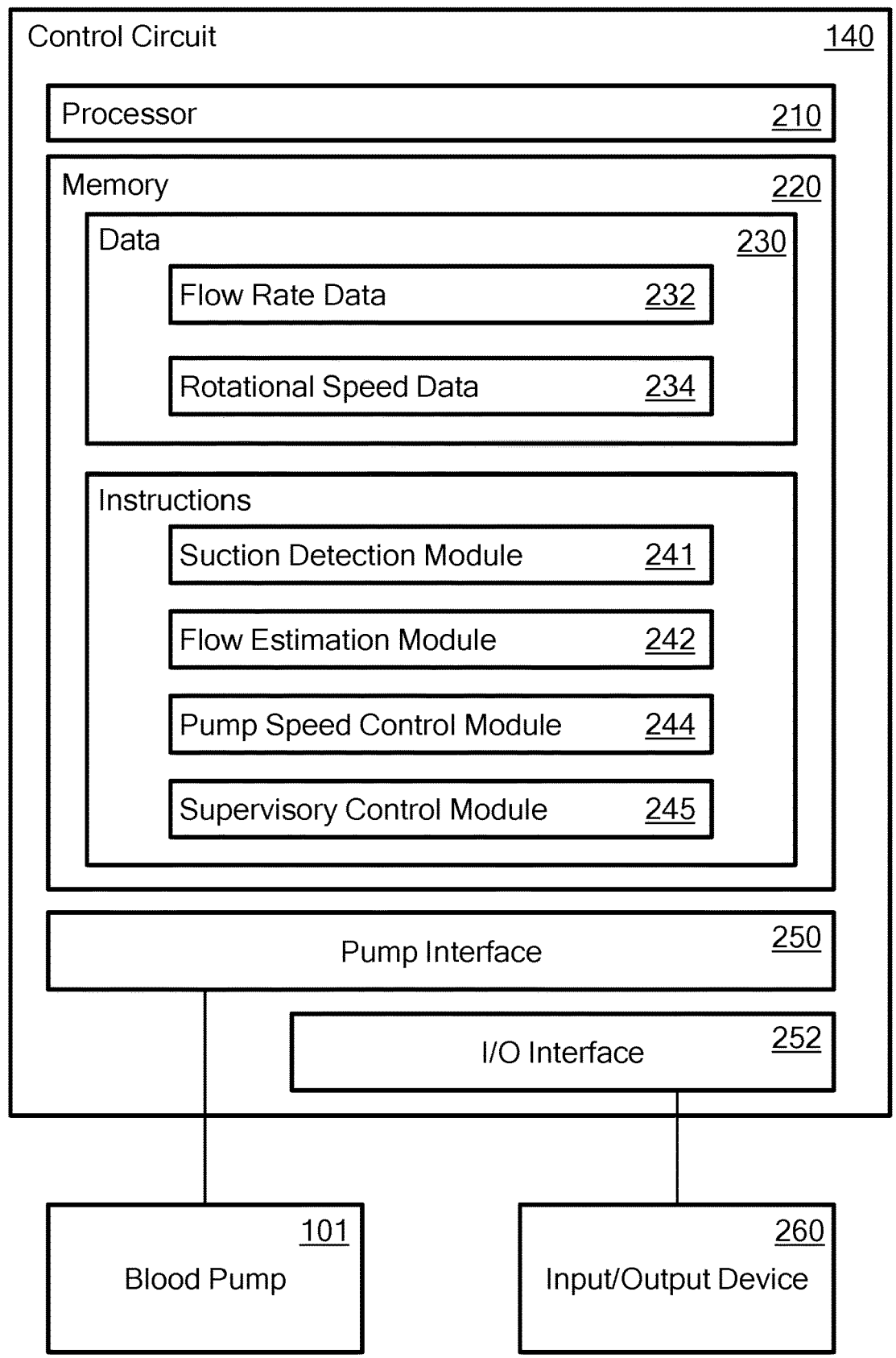
FIG. 3 is a block diagram of the control circuit of the VAD of FIG. 1.

The control circuit 140 monitors and further controls operation of the pump 101. The control circuit functions may be implemented at least in part by a general-purpose processor, as shown in the example implementation of FIG. 3. As shown, the control circuit 140 is implemented using a processor 210, a memory 220, data 230, instructions 240, and a pump interface 250. Interface 250 may include components such as power semiconductors connected to the coils of the pump, as well as one or more sensors for detecting voltages on the pump coils. The control circuit 140 may optionally include an I/O interface 252 that connects the control circuit 140 to one or more I/O devices 260 adapted to input information into the control circuit, output information from the control circuit, or both. The interface 250 may be an analog interface (e.g., audio interface) or a digital interface, such as Bluetooth, TCP/IP, Wi-Fi, and others. Where the control circuit is implemented in an implantable structure adapted to be disposed within the body of the patient, the I/O interface 252 may include known elements for communicating signals through the skin of the patient. Merely by way of example, the I/O device 260 may be a speaker, a light, a display screen, a communications terminal (e.g., computer, cell phone), a keyboard, or any other type of input and/or output device.

Memory 220 stores information accessible by processor 210, including instructions 240 that may be executed by the processor 210. The memory also includes data 230 that may be retrieved, manipulated, or stored by the processor 210. The memory may be of any type capable of storing information accessible by the processor, such as a hard-drive, memory card, ROM, RAM, DVD, CD-ROM, write-capable, and read-only memories. The processor 210 may be any well-known processor, such as commercially available processors. Alternatively, the processor may be a dedicated controller such as an ASIC.

Data 230 may be retrieved, stored, or modified by processor 210 in accordance with the instructions 240. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations), or information that is used by a function to calculate the relevant data. The instructions stored in the memory may include one or more instruction sets or modules for performing certain operations. One such module may be a flow estimation module 242 for performing the steps required to estimate a flow rate of blood through the pump. Another such module may be a pump control module 244 for controlling the speed of the pump speed control module. Another such module may be a suction detection module for determining the presence of a suction condition and taking actions in response to the same.

Although FIG. 2 functionally illustrates the processor and memory as being within the same block, it will be understood that the processor and memory may actually comprise multiple processors and memories that may or may not be stored within the same physical housing. The memory may include one or more media on which information can be stored. In one configuration, the medium holding the instructions retains the instructions in non-transitory form. Some or all of the instructions and data may be stored in a location physically remote from, yet still accessible by, the processor. Similarly, the processor may actually comprise a collection of processors that may or may not operate in parallel.

The control circuit 140 is coupled to the pump and is configured to collect pump data. The pump data includes speed of rotation of the pump's rotor and amount of current used to drive the pump. For example, the control circuit 140 may be configured to apply pulse width modulated voltage to individual coils in sequence to provide the rotating magnetic field that turns the rotor. At a given time in the sequence, one or more of the coils is in an idle state with no applied voltage. The moving magnets of the rotor induce voltages in the idle coil, referred to as "back EMF." The pump interface 250 may be arranged to sample the back EMF in one or more of the coils during its idle state, and to supply the resulting sequence of samples to the processor. The instructions in pump speed control module 244 may cause processor 220 examine these samples to detect a zero crossing or other recurring feature of the back EMF waveform, and to determine the time between recurrences. This time is inversely proportional to the speed of rotation of the rotor. The processor repeatedly calculates the pump speed at a repetition rate many times the heart rate of the patient, i.e., a repetition time much shorter than a cardiac cycle. For example, the processor may determine the speed of the pump at a repetition rate of about 20 Hz or more and record the resulting sequence of rotational speed data 234. In this embodiment, one or more of the coils of the pump motor serve as sensors for determining the rotational speed of the rotor. In other embodiments, one or more separate sensors such as sensing coils separate from the rotor or Hall effect devices may be used to detect magnetic field changes associated with rotation, and the signals from these sensors may be used to detect rotational speed. In still other embodiments, other known techniques may be used for detecting the rotational speed.

The pump speed control module 232 also includes instructions that cause the processor to adjust the pump interface 250 so as to maintain the rotational speed of the pump at a set speed. Stated another way, these instructions cause the processor to act as an element of a rotor speed control circuit. For example, if the rotational speed is below the set speed, the processor may instruct the pump interface to increase the rotational speed by increasing the current in the coils, as by increasing the duty cycle of the pulse width modulated voltages applied to the coils. The processor may execute a proportional-integral-derivative ("PID") feedback control scheme. In such a scheme, the processor compares the rotational speed of the pump to the set speed and generates an error signal that includes a proportional component representing the difference between the actual speed and the set point; an integral component representing the integral of the difference, and a derivative component representing the rate of change in the difference. The control circuit 140 has a small but finite response time to a change in the actual speed. As used in this disclosure, the term "response time" denotes the time from an instantaneous step change in actual speed that causes the actual speed to deviate from the set point to the time 90% of the deviation is corrected. For example, the response time may be on the same order as the repetition time between successive speed determinations or greater. In this embodiment, the set speed is constant during normal operation. The set speed may be changed by commands input to the control by circuit through I/O device 260, or by actions taken by supervisory control module 245. For example, the supervisory control module may be responsive to physiological changes as, for example, changes in the patient's level of activity.

In addition, the control circuit is operable to collect flow rate data points 232 indicative of a flow rate of blood through the pump. The instructions in flow rate estimation module 242 may cause the processor to estimate the flow rate based on data including the current in the coils, the speed of the rotor and the acceleration of the rotor of the pump, and the viscosity of the patient's blood. The speed and acceleration may be taken from the rotational speed data 323 discussed above. The viscosity of the patient's blood normally may be input to the control system as a constant (e.g., based on the patient's hematocrit level), or may be estimated as, for example, by measuring the deceleration of the pump responsive to momentary interruption of power supply to the pump as described in U.S. Pat. No. 8,961,390, the disclosure of which is incorporated by reference herein. Such measurements may be repeated periodically as, for example, hourly or daily. The current in the coils is directly related to the duty cycle of the pulse width modulated voltage applied to the coils by the pump interface and can be acquired from the pump interface. Alternatively, the current in the coils can be acquired by a current-sensitive sensor (not shown) electrically connected to the coils. As described in U.S. Pat. No. 8,897,873, the disclosure of which is incorporated by reference herein, the instantaneous flow through the pump can be estimated based on this information. Using such a model results in the estimate having a dynamic range of about 15 Hz.

In other examples, other parameters indicative of flow may be used, and/or different calculations may be employed, to estimate a flow rate of blood. Alternatively, flow rate data points may be gathered using direct measurements, such as with an ultrasonic flow meter.

The suction detection module 241 includes instructions that cause the processor to periodically examine the rotational speed data 234 and determine a maximum and minimum speed during a series of speed measurement intervals. Each interval may be slightly longer than the maximum cardiac cycle time as, for example, about 2 seconds. For each interval, the processor determines a speed range by subtracting the minimum rotational speed from the maximum rotational speed. The processor compares the speed range for each speed measurement interval with a range limit. The range limit may be a fixed parameter stored in memory during setup of the system, or may be a function of the set speed prevailing during the measurement interval as, for example, a fixed percentage of the set speed. If the speed range is above the range limit, the processor issues a speed range signal as, for example, by setting a speed range flag to a "true" condition. If not, the processor sets the speed range flag to a "false" condition.

Figure 4:
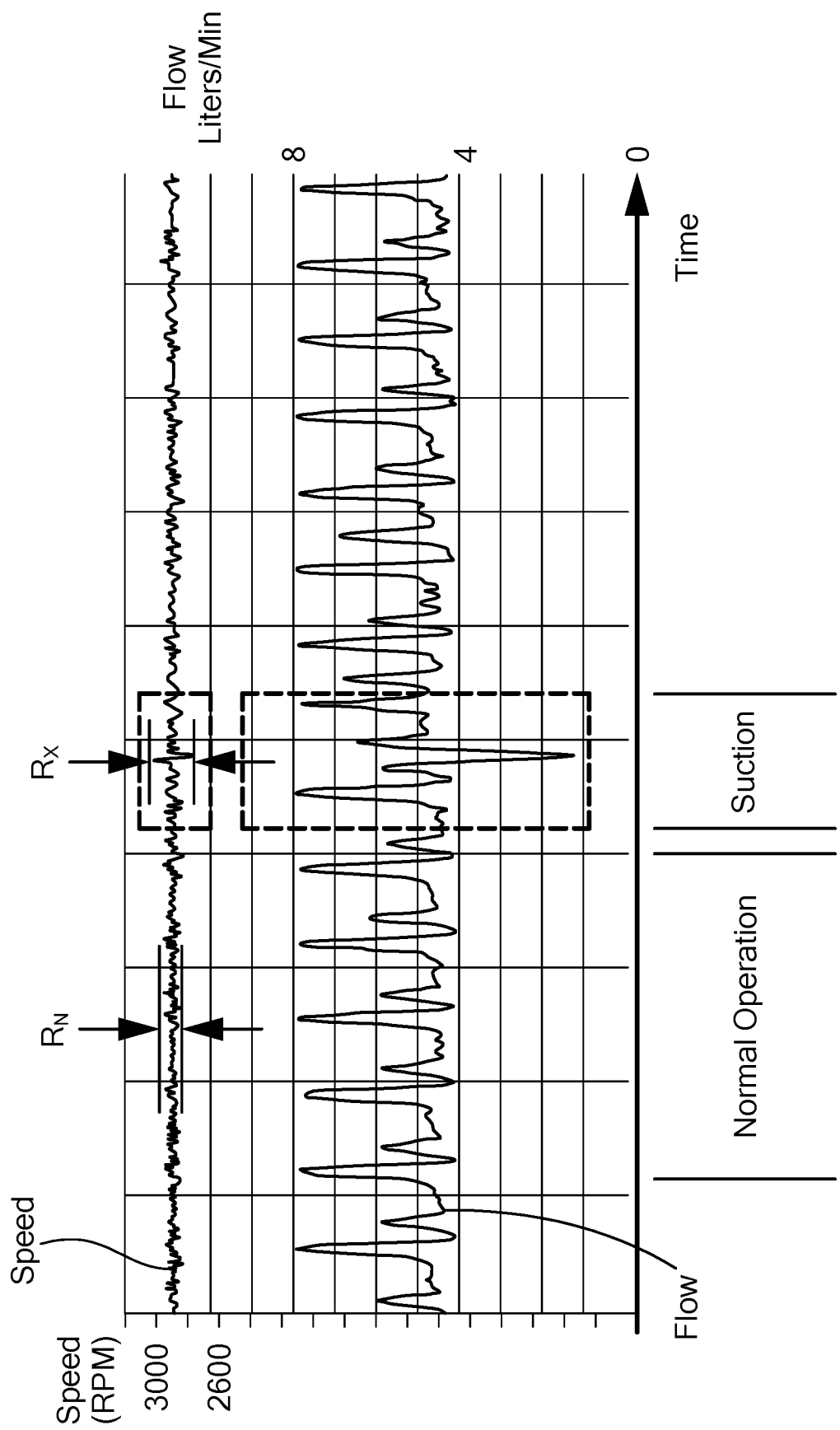
FIG. 4 is a graph depicting pump speed and flow rate.

The speed range for each speed measurement interval represents the interaction between the rotor speed control circuit discussed above and physical events which tend to change the rotor speed. As best seen in FIG. 4, during normal operation the flow through the pump changes during each cardiac cycle due to the pumping action of the heart. These changes tend to increase and decrease the speed of the rotor, but the control circuit maintains the rotor speed within a relatively narrow normal range RN. However, during a suction condition, the flow changes to a greater extent and at rapid rates. Although the present invention is not limited by any theory of operation, these changes in flow may be due to blockage of the pump inlet associated with collapse of the ventricle. These changes in flow tend to cause greater and more rapid changes in the rotor speed. Although the control circuit counteracts this tendency, the net result is that the rotor speed varies over a greater, abnormal range RX. The range limit desirably is greater than the normal range RN but less that the expected abnormal range RX during suction conditions, so that a range above the range limit is indicative of a suction condition. The normal range RN and the abnormal range RX depend in part on the characteristics of the control circuit. For example, a control circuit with a slower response time would yield greater normal and abnormal ranges. The appropriate range limit for a VAD of a given design, with a control circuit of a given design can be determined by review of operational data.

Although a speed range above the range limit is indicative of a suction condition, a speed range above the range limit may also occur in other conditions as, for example, where the patient's blood flow has very high pulsatility or during certain cardiac arrhythmias.

The suction detection module also includes instructions that cause the processor to examine the flow rate data during one or more cardiac cycles. The processor maintains a moving average of the flow rate over time. This moving average typically includes flow rate data from a plurality of cardiac cycles. For example, the processor may maintain a moving average consisting of the average value of a set consisting of the last N flow rate estimates, i.e., the sum of the last N flow rate estimates divided by N. N is an integer that desirably is greater than the number of flow rate estimates obtained during a single cardiac cycle. Each time a new flow rate estimate is derived by the flow estimation module as discussed above, the processor deletes the oldest value in the set, adds the new value to the set, and computes a new value of the moving average.

The processor compares each flow rate estimate to the value of the moving average at the time of such flow rate estimate, i.e., the first value of the moving average computed using that flow rate estimate as part of the set of N values. Thus, the processor determines whether each flow rate estimate is above or below the moving average.

The processor determines the beginning of a cardiac cycle by examining the results of this comparison. The time when the flow rate rises above the moving average is taken as the beginning of systole and as the end of one cardiac cycle and the beginning of the next cardiac cycle. Thus, if the last previous flow rate estimate was below the moving average, and a new flow rate estimate is above the moving average, the processor recognizes the time of the new estimate as the beginning of a new cardiac cycle.

The processor counts the number of flow rate estimates during the entire cardiac cycle and also counts the number of flow rate estimates which were above the moving average during the cardiac cycle. Because the flow rate estimates are acquired periodically, at a uniform rate, the number of flow rate estimates during the cardiac cycle is directly proportional to the total duration of the cardiac cycle. Likewise, the number of flow rate estimates above the moving average is proportion to the time during which the flow rate is above the moving average.

For each cardiac cycle, the system divides the number of flow rate estimates within the cycle above the moving average by the number of flow rate estimates in the cardiac cycle to arrive at a parameter referred to herein as the "duty parameter." The duty parameter is directly related to the portion of the cardiac cycle during which the flow rate was above the moving average.

The processor compares the duty parameter for each cardiac cycle with a set duty limit. As explained below, a duty parameter above the duty limit is indicative of a suction condition.

Figure 5:
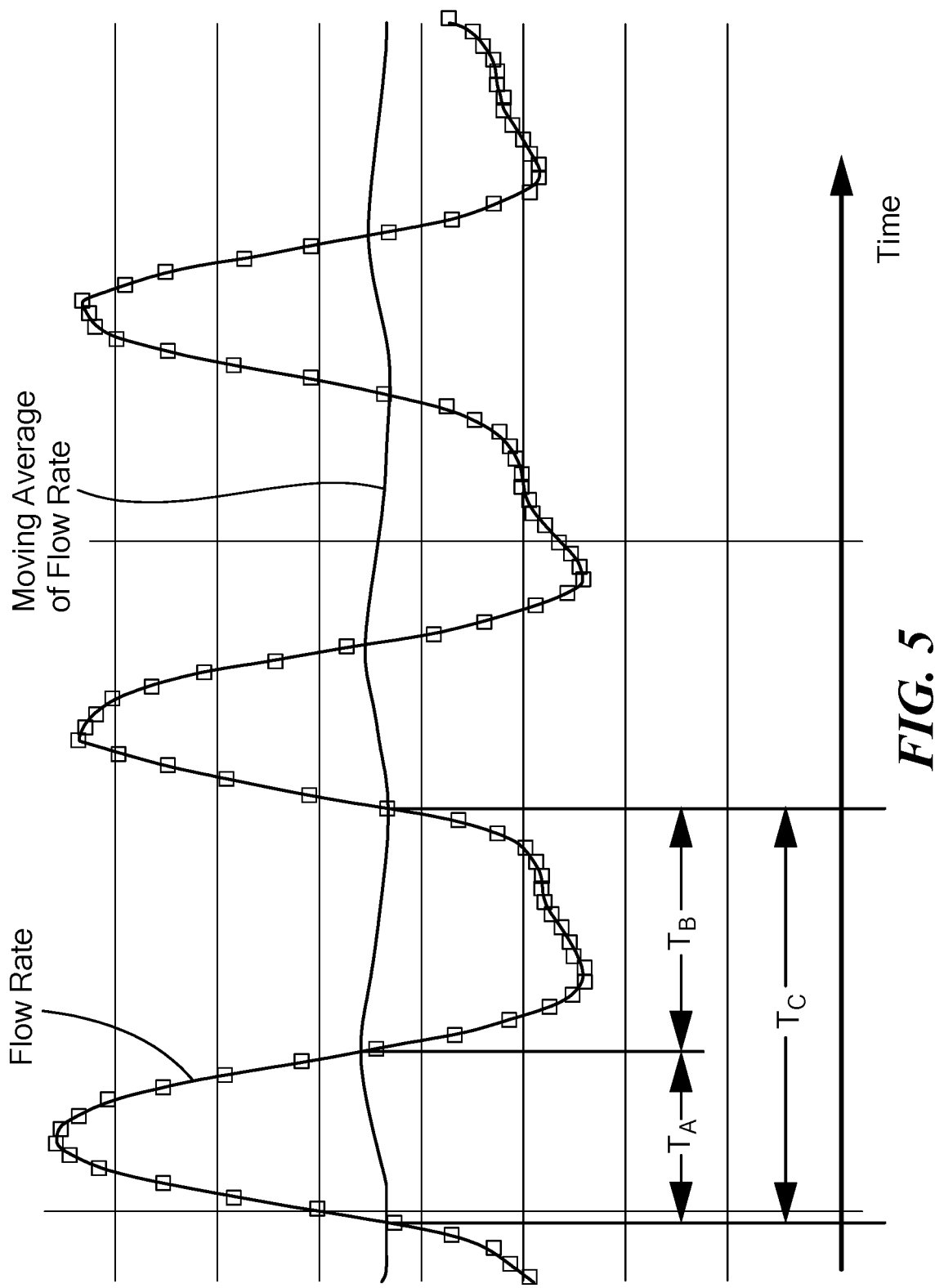
FIG. 5 is a graph depicting flow rate and a moving average flow rate during normal operation.

Referring now to FIG. 5, the flow rate during normal operation remains above the moving average for a relatively brief time TA at the beginning of each cycle and is below the moving average for a longer time TB near the end of each cycle. The total duration of the cycle is indicated by TC. Thus, the duty parameter is less than 0.5. Each flow rate estimate is indicated by a small square on the flow rate curve. In the example shown in FIG. 5, there are 31 flow rate estimates during the entire cardiac cycle. Of these, 13 estimates are above the moving average (i.e., during TA), whereas 18 were below the moving average (i.e., during TB). The duty parameter is TA/TC, or 13/31, i.e., about 0.42 or 42%.

Figure 6:
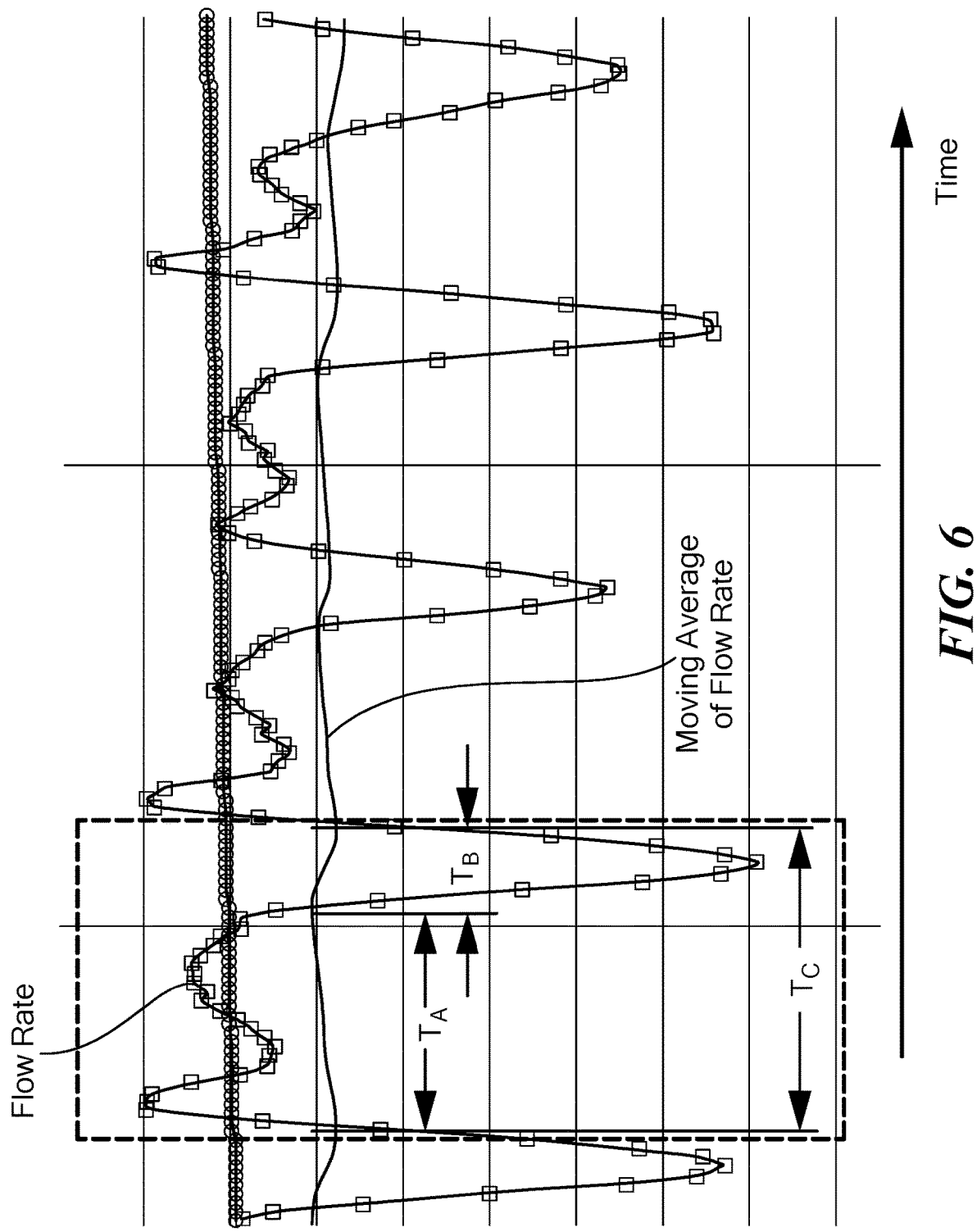
FIG. 6 is a graph similar to FIG. 5, but depicting a suction condition.

Referring now to FIG. 6, by contrast, in a suction condition as depicted in FIG. 6, the time TA above the moving average is prolonged and constitutes a greater proportion of the entire cardiac cycle TC, whereas the time TB below the moving average is shortened. In the particular example shown, there are 33 flow rate estimates in the entire cardiac cycle. Of these, 24 flow rate estimates are above the moving average (i.e., during TA), whereas 9 are below the moving average (i.e., during TB). The duty parameter TA/TC is 24/33, i.e., about 0.73 or 73%.

The duty limit in this example desirably is set at a value above that which occurs in normal operation, and below that which occurs during suction conditions as, for example about 0.5 to about 0.6. If the duty parameter is above the duty limit, the processor issues a duty signal representing the fact that that the duty parameter is indicative of a suction condition as, for example, by setting a duty flag to a "true" condition. If not, the processor leaves the duty flag in a "false" condition.

Figure 7:
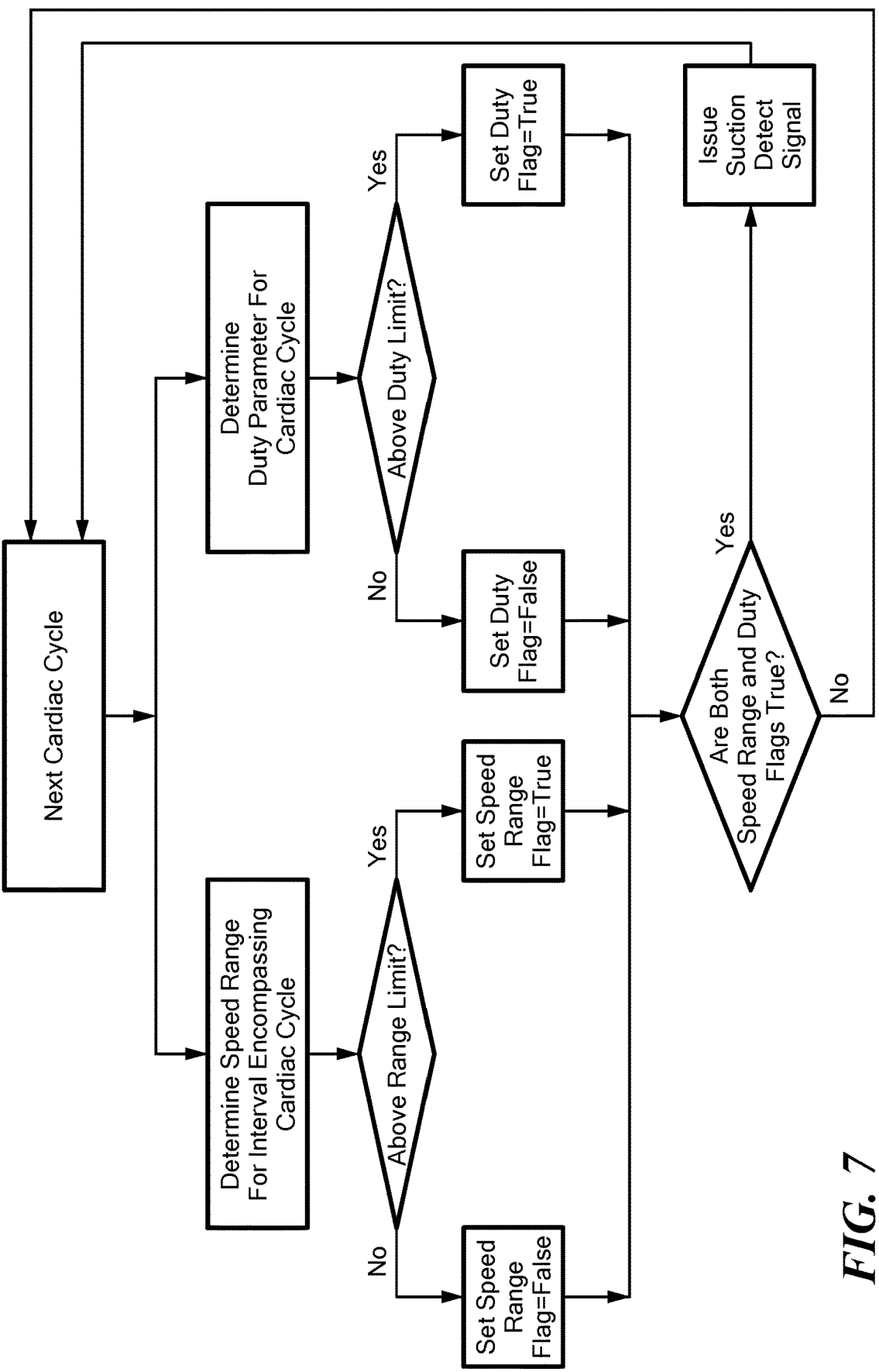
FIG. 7 is a flow chart depicting a portion of a method according to one embodiment of the disclosure.

Referring now to FIG. 7, for each cardiac cycle, the processor checks whether the duty signal has been generated for that cardiac cycle and also checks whether the range signal has been generated for an interval which substantially or completely overlaps that cardiac cycle. For example, the processor may check if the duty flag was set during the last completed cardiac cycle, and if the range signal was set for the speed measurement interval ending immediately after the end of such cycle. If both conditions are true, the processor issues a suction detection signal indicating that a suction condition exists. The suction detection signal may be sent through the I/O interface 252 (FIG. 3) and converted to a human-perceptible signal such as a visual indication on a display, an audible signal or the like, or may be transmitted through the I/O interface to a remote monitoring device. Alternatively or additionally, the processor may react to the suction detection signal by altering operation of the pump according to instructions in supervisory control module 245. For example, the processor may reduce the set speed of the pump and then check to determine if such reduction eliminates the suction condition in subsequent cardiac cycles. If the suction condition has been cleared, the processor may then increase the set speed gradually while continuing to monitor for recurrence of the suction condition. Routines for adjusting the set speed of a rotary pump responsive to a suction condition are disclosed, for example, in the aforementioned '048 Publication and '413 Publication.

The increase in the duty parameter discussed above is strongly associated with the occurrence of a suction condition. For example, the duty parameter typically does not increase above the duty limit during arrhythmias, during conditions of high or low pulsatility, or during changes in pump speed commanded by the supervisory control system or manual inputs. Because the pump speed range is used in combination with flow data in the system and methods discussed above, the suction detect signal will not be generated even if the speed range signal is erroneously set to true. In operation, using speed and flow data previously recorded during actual operation of the VAD with real patients and including known suction events, the system was able to identify every known suction event, and thus exhibited 100% sensitivity. The system did not issue any suction detect signals in the absence of a known suction event and thus exhibited 100% specificity.

Moreover, the system is extremely simple both in concept and in implementation. There is no need to maintain and update values based on computations or data from previous cycles. The suction detect signal is generated based on data from a single speed detection interval and a single cardiac cycle. This allows the system to issue the suction detect signal promptly at the start of a suction condition, so that corrective action can be taken promptly.

The system and method discussed above can be varied in many ways. In the system and method as discussed above, the moving average flow rate serves as a crossover value for determination of the duty parameter. The duty parameter represents the proportion of the cardiac cycle duration during which the flow rate is above this crossover value. In other embodiments, the crossover value may be another flow rate. For example, the crossover value may be a function of the moving average flow rate as, for a multiple of the moving average flow rate such as 1.1 times the moving average or 0.9 times the moving average.

In the embodiments discussed above, the duty parameter is equal to the time TA above the crossover value divided by the duration of the cardiac cycle, and thus is directly proportional to TA. However, the duty parameter can be calculated in many other ways provided that the duty parameter is a function of any two or more of TA, TB and TC. For example, the duty parameter can be calculated as the time TB below the crossover value divided by the duration of the cardiac cycle. In this instance, the duty parameter would vary inversely with TA, so that a value of the duty parameter less than a duty limit would be indicative of a suction condition. In yet another variant, the duty parameter could be taken as the difference between time above the crossover value and time below the crossover value, i.e., (TA−TB) or vice-versa (TB−TA). In these embodiments, the duty parameter is not proportional to TA or to TA/TC, but nonetheless represents the proportion of time during the cardiac cycle during which the flow rate is above the crossover value. Stated another way, the duty parameter need not vary linearly with TA/TC. In the embodiments discussed above, the duty parameter is determined over a single cardiac cycle. However, the duty parameter can be determined over a plurality of complete cardiac cycles as, for example, by averaging duty parameters determined from plural cycles or, equivalently, calculating the duty parameter based on the sums of two or more of TA, TB and TC for the plural cycles.

In the embodiments discussed above, the speed range is calculated over intervals that are determined without regard for cardiac cycles. Because each interval is longer than a single cardiac cycle, each interval encompasses a complete cardiac cycle and also includes some data collected during one or more other cycles. In a variant, the speed range can be determined over intervals corresponding exactly to cardiac cycles. For example, each speed measurement interval may begin when the beginning of a cardiac cycle is recognized based on the flow rate rising above the moving average and end when the next cardiac cycle begins.

In the embodiments discussed above, the speed pump speed data and flow data are each converted to a binary indication, i.e., true or false, and combined by an "and" operation, so that the suction detect signal is generated only if both are true. However, either or both of these indications can be provided in a format that conveys additional information. For example, the duty parameter and the measured speed range can be provided as multi-bit values, and can be combined with one another in a more complex manner. For example, one of these values may serve as a row address of a two-dimensional lookup table, whereas the other value serves as the column address. Each cell of the lookup table may store a binary value, i.e., "no suction" or "suction," so that the suction detect signal is generated only when the row and column addresses point to a cell with the "suction" value. In a further variant of such a scheme, each cell of the lookup table may store a multi-bit number indicating a probability that a suction condition is present. In a further variant, the measured speed range may be compared with the range limit as discussed above, and the result may be output as a multi-bit value that denotes the sign and magnitude of the difference. Likewise, the duty parameter may be compared to the duty limit, and the result may be output as a multi-bit value the sign and magnitude of the difference. These results may be used in a lookup table scheme. Alternatively, these results may be combined as, for example, by addition or multiplication, to yield a composite value, and the composite value may be compared to a threshold value so that the suction signal is generated only if the composite value exceeds the threshold.

In a further variant, the range limit, the duty limit, or both may be based on data from previous measurement intervals or cardiac cycles. For example, the range limit may be a selected based in whole or in part on the speed ranges observed in previous speed measurement intervals. The duty limit may be based in whole or in part on the duty parameters measured in previous cardiac cycles. However, such an arrangement is generally less preferred.

As discussed above, the change in the duty parameter is strongly associated with the presence of a suction condition. Thus, the duty parameter can be used by itself as the sole indicator of the presence or absence of a suction condition. In one such embodiment, the suction detect signal is generated whenever the duty parameter exceeds the duty limit. Alternatively, the decision to issue the suction detect signal can be based on the duty parameter can be used in conjunction with other information which is indicative, to at least some degree, of the presence or absence of a suction condition.

The speed range information discussed above can be combined with information other than the duty parameter discussed above so as to provide an indication as to whether or not a suction condition exists which has greater specificity than that afforded by speed range alone. For example, information derived from flow rate data other than the duty parameter can be used in conjunction with the speed range discussed above. In one such example, the speed range determined during one or more measurement intervals may be combined with flow rate data such as the waveform index taught in the '048 Publication or with flow rate threshold information as taught in the '413 Publication, and a suction detect signal may be generated if both the speed range and the flow rate information are indicative of a suction condition.

The pump depicted in FIGS. 1 and 2 and discussed above is a centrifugal pump with an impeller arranged so that blood flows substantially in a radial direction across the impeller. In other examples, the blood pump may be an axial flow pump, such as that used in the MVAD® ventricular assist device, also manufactured by HeartWare Inc. As further described in U.S. Patent Application Publication No. 2012/0245681, the disclosure of which is incorporated by reference herein, in an axial flow blood pump, the impeller drives the blood in a direction generally parallel to the axis of the impeller. Still other pumps have impellers arranged to drive the blood in mixed axial and radial flow. Any of these blood pumps may be used.

The operations described above do not have to be performed in the precise order described. Rather, various operations can be handled in a different order or simultaneously. It should also be understood that these operations do not have to be performed all at once. For instance, some operations may be performed separately from other operations. Moreover, operations may be added or omitted. As these and other variations and combinations of the features discussed above can be used, the foregoing description should be taken as illustrating, rather than as limiting, the present disclosure.

What is claimed is:

1. A method of detecting a suction condition during operation of a rotary blood pump with an inlet connected to a ventricle of a heart of a patient, an outlet connected to an artery of the patient, a rotor, and a control circuit configured maintain the rotor at a set rotational speed, the method comprising:
    (a) measuring the rotational speed of the rotor at a plurality of times during each of a plurality of speed measurement intervals;
    (b) determining a speed range between a minimum measured speed and a maximum measured speed during each of the plurality of speed measurement intervals;
    (c) deriving at least one additional parameter relating to the operation of the blood pump, the additional parameter being a number of flow rate estimates during one or more cardiac cycles above a moving average flow rate divided by the number of flow rate estimates during the one or more cardiac cycles; and
    (d) generating a suction detection signal if both (i) at least one determined speed range is above a speed range limit and (ii) the at least one additional parameter is indicative of a suction condition.

2. The method of claim 1, wherein the speed range limit is a function of the set speed during a respective one of the plurality of speed measurement intervals.

3. The method of claim 1, further comprising determining an error signal based on at least one from the group consisting of a difference between the measured speed and the set speed, an integral of such difference over time, and a first derivative of such difference.

4. The method of claim 1, wherein generating the suction detection signal includes generating the suction detection signal if (i) occurs during one speed measurement interval at least partially encompassing a cardiac cycle of the patient's heart and (ii) is occurs during the same cardiac cycle of the patient's heart.

5. The method of claim 1, further comprising repeatedly determining an average flow rate, and wherein a crossover flow rate is a function of the average flow rate.

6. The method of claim 5, wherein the crossover flow rate is equal to the average flow rate.

7. The method of claim 1, further comprising comparing the additional parameter to a duty limit constant, and wherein the additional parameter varies directly with the proportion of time the flow rate is above a crossover flow rate.

8. The method of claim 1, further comprising adjusting the set rotational speed of the rotor responsive to the suction detect signal.

* * * * *